United States Patent
Gombrich et al.

[19]

[11] Patent Number: 5,999,844
[45] Date of Patent: Dec. 7, 1999

[54] METHOD AND APPARATUS FOR IMAGING AND SAMPLING DISEASED TISSUE USING AUTOFLUORESCENCE

[75] Inventors: Peter P. Gombrich, Chicago; Norman J. Pressman, Glencoe; Richard A. Domanik, Libertyville, all of Ill.

[73] Assignee: AccuMed International, Inc., Chicago, Ill.

[21] Appl. No.: 08/845,261

[22] Filed: Apr. 23, 1997

[51] Int. Cl.[6] .................................................. A61B 6/00
[52] U.S. Cl. ........................ 600/476; 600/160; 600/109; 600/477
[58] Field of Search .................................... 600/476, 473, 600/310, 160, 178, 182, 109, 477; 250/458.1, 461.2, 484.2

[56] References Cited

U.S. PATENT DOCUMENTS

| | | | |
|---|---|---|---|
| 4,718,417 | 1/1988 | Kittrell et al. . | |
| 4,905,670 | 3/1990 | Adair . | |
| 4,930,516 | 6/1990 | Alfano et al. ............................ | 600/477 |
| 5,042,494 | 8/1991 | Alfano ..................................... | 600/477 |
| 5,131,398 | 7/1992 | Alfano et al. ............................ | 600/476 |
| 5,507,287 | 4/1996 | Palcic et al. ............................. | 600/317 |
| 5,596,992 | 1/1997 | Haaland et al. . | |
| 5,623,932 | 4/1997 | Ramanujam et al. . | |
| B1 4,930,516 | 8/1998 | Alfano et al. ............................ | 600/477 |

FOREIGN PATENT DOCUMENTS

WO 96/28084  9/1996  WIPO .

OTHER PUBLICATIONS

International Search Report in PCT/US98/21710, dated Jan. 26, 1999.

*Primary Examiner*—Brian L. Casler
*Attorney, Agent, or Firm*—McDonnell Boehnen Hulbert and Berghoff

[57] ABSTRACT

A method and apparatus for imaging body tissue utilizing autofluorescence. The apparatus includes an endoscope having a distal end, proximal end and a light processing unit located at the proximal end of the endoscope. The light processing unit accepts light in a spectral region from a light source and directs the light through the endoscope to the tissue located at the distal end of the endoscope. The light excites autofluorescence in the tissue. Optics located in the distal end of the endoscope collect the excited autofluorescence in a spatially resolved manner and routes it to the light processing unit which separates the emitted light from any reflected excitation light. A plurality of imaging detectors receive the emitted light. Each imaging detector is responsive to light in a different spectral band such that an image is generated and interpreted according to a plurality of independent measurements. An apparatus for sampling tissue includes an endoscopic device having a sampling device. The sampling device is capable of taking a plurality of tissue samples. Captive units are in communication with the sampling device such that each tissue sample is deposited in a separate captive unit.

26 Claims, 2 Drawing Sheets

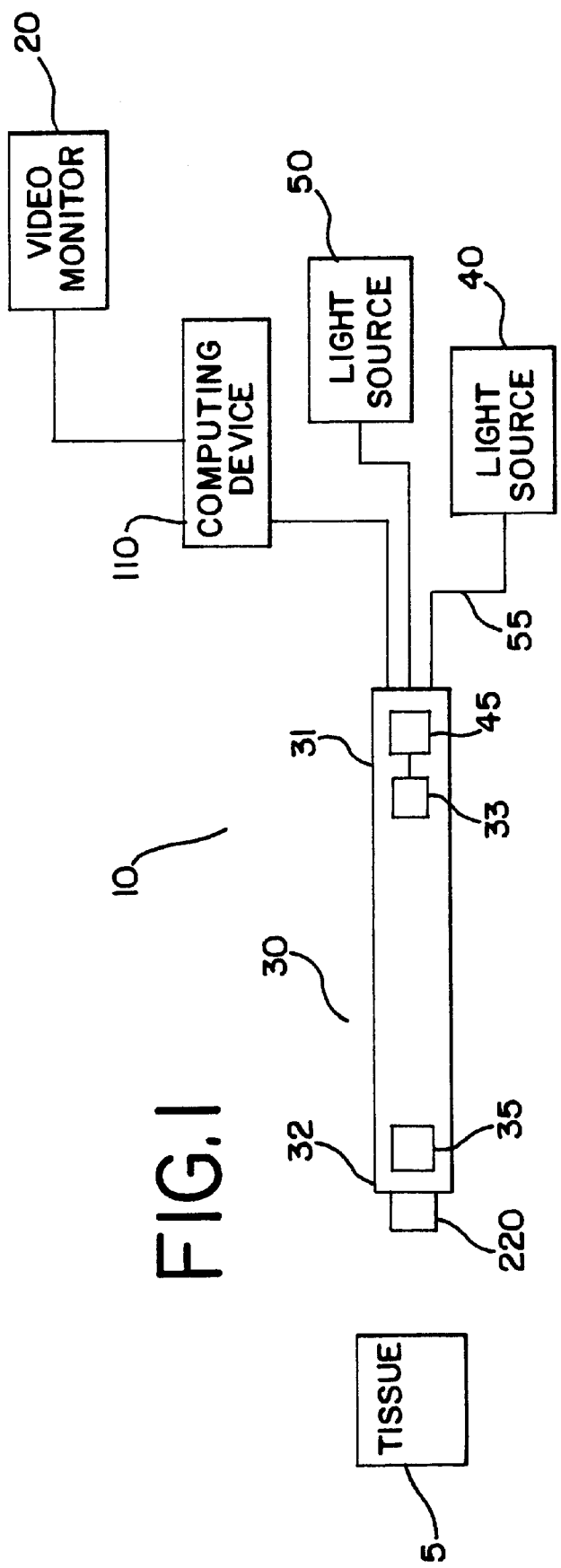
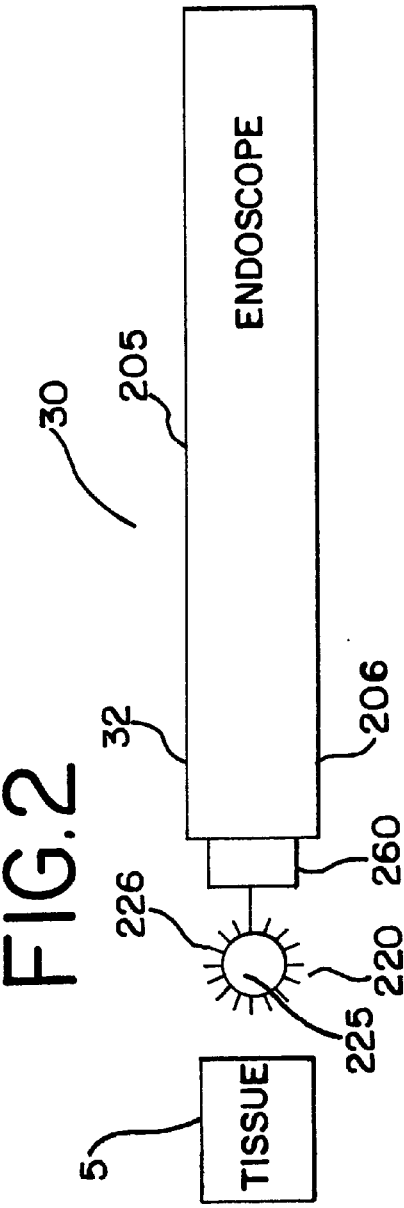

METHOD AND APPARATUS FOR IMAGING AND SAMPLING DISEASED TISSUE USING AUTOFLUORESCENCE

BACKGROUND OF THE INVENTION

A. Field of the Invention

The present invention relates to an apparatus and method for imaging bodily tissue by using autofluorescence. More particularly, the present invention relates to an endoscopic apparatus and method for imaging and sampling bodily tissue using autofluorescence techniques.

B. Description of Related Art

Cervical cancer often begins as a precancerous lesion on the cervix (i.e., the outer end of the uterus) and is called cervical intraepithelial neoplasia (CIN). The lesion can deepen over a period of years and if left untreated can become an invasive cancer. A Pap smear test is currently a common method of providing a type of screening for cervical cancer. The test involves taking a sample of cells from the cervix, and sending the sample to a laboratory to be analyzed. Test results usually take two or three weeks to complete.

If the laboratory analysis determines that abnormal cells are detected from a first Pap test, a follow up test it typically performed. A second abnormal Pap smear will often prompt a colposcopic examination wherein the cervix is examined usually with a low-power stereo microscope. During colposcopy, suspect abnormal tissue is often biopsied and again sent to a laboratory for analysis. Because patients must often wait another two to three weeks for these results, a heightened period of anxiety and fear for the women and their families is created. Often, the first and second abnormal Pap smear result from false positive test results. Therefore, oftentimes, when a tissue sample has been biopsied, the sampled tissue was incorrectly determined to be cancerous and did not need to be removed. Spectroscopic autofluorescence, a minimally invasive procedure for analysis of cervical cytological, has been used to decrease a number of the problems normally associated with Pap smear tests.

Spectroscopic methods for differentiating cervical neoplasia from normal cervical tissue in vivo can be used to detect abnormal cells on the outside of the cervix. Typically, a fluorescence spectroscope has optical fibers at the end of a small probe which illuminate areas of the cervix. Suspect tissue is exposed to ultraviolet and visible laser or lamp light, causing substances naturally present in the tissue to fluoresce. The specific wavelength or signature of the light absorbed and emitted by cervical tissue is analyzed. The fluorescence spectra is then measured and compared at different intensities and wavelengths since abnormal or cancerous tissues consistently display different results from normal or non-cancerous tissue. Typically, a computer algorithm analyzes the fluorescence spectrum and assesses the degree of cell abnormality.

Generally, there are two types of fluorescence measurement techniques: the first being emission spectroscopy and the second being excitation spectropscopy. In emission spectroscopy, the exciting light is kept at a fixed wavelength and the emitted fluorescent intensity is measured as a function of the emitted wavelength. In excitation spectroscopy, the emission wavelength is kept fixed and the fluorescence intensity is measured as a function of the excitation wavelength.

Both emission and excitation spectra measurements have limitations. For example, both types of spectra measurements analyze only a single parameter to determine cell abnormality. The nature of the human tissue, however, is such that the application of any one single method produces a large amount of data, most of which is extraneous to the intended measurement. A primary reason for this situation is that tissues contain an extensive and diverse assortment of fluorescent species. Many of the species are present in high concentrations and have excitation bands distributed throughout the ultraviolet and the visible spectra regions.

Another limitation is that the emission band of one fluorophore may overlap the excitation band of another fluorophone, consequently leading to energy transfer between the emission and excitation bands. Consequently, emissions from one fluorophore could possibly excite another fluorophore. The net effect is that optically exciting a tissue sample at almost any wavelength in the ultraviolet or visible wavelength regions causes tissue autofluorescence over a broad spectral range. As these emissions are typically composed of contributions from multiple fluorophores, utilizing a single analytical parameter makes the autofluorescence spectrum complex and problematic to solve. Consequently, a robust discrimination between tissue states is often difficult to obtain.

Another limitation of typical fluorescence measurement techniques is that they cannot be readily combined with an apparatus or method for taking a biopsy. In other words, once an abnormal tissue area is detected, samples from this particular suspect area cannot be simply, quickly and accurately taken. With current devices utilizing fluorescent measurement techniques, after locating the abnormal area, the endoscope must be withdrawn from the patient. Once the endoscope is withdrawn, the Pap smear specimen can then be taken as a blind sample. Typically, there is no correlation between where on the cervix the sample is taken and where the suspect tissue was identified. Taking a blind sample, therefore, often results in samples being taken from normal areas or perhaps even areas which have not been previously investigated. Usually, the sample is also taken by relatively imprecise sampling devices such as brushes, scraper devices or the like.

Once the sample has been taken and withdrawn from the body, the specimen is typically smeared onto a microscope slide. This is often done by the physician performing the test. The slide is then submitted to a remote laboratory for cytopathological microscopic examination. Pertinent patient data must be sent along with the slide including the medical history, day in menstrual cycle, family history and other known risk factors. Gathering and collating these patient data, which are critical to the proper evaluation of a specimen, is a time-consuming, expensive, inefficient and labor-intensive process. The laboratory administrative personnel who gather such data are also responsible for manually recording the results of the Pap smear tests and ensuring that both the slide and paperwork provided to the cytotechnologist relate to the same patient. As the complexity of testing, analyzing, handling and transporting the Pap smear samples increases, the probability for a false positive, a false negative or sample contamination increases.

The typical Pap smear test has a number of other disadvantages For example, in almost every instance where a slide specimen is produced, the slide is forwarded to a laboratory. No preliminary analysis to eliminate possible unnecessary laboratory testing is conducted. This increases the cost of performing a Pap smear since there is no preliminary determination as to the possibility of normality or absence of abnormality. Moreover, because the sampling is taken "blind", there is typically no assurance as to whether the suspect abnormal cells have in fact been sampled. Oftentimes, only after having forwarded the sample to the testing facility and waiting two to three weeks is it eventually determined that another sample must be taken. Incidents of poor sample or slide preparation are also common because of the large amount of human interface with each specimen slide. Moreover, because slides are often sent to a location remote, there is an increased risk that the sample may become lost, broken or contaminated. The complexity of maintaining a secure and sterile transporting medium further increases the cost of sample transport. In addition, there is a psychological disadvantage in having to wait up to two weeks or longer for the test results to either confirm or rebut a primary abnormal reading.

SUMMARY OF THE INVENTION

The present invention relates to an apparatus and method for imaging body tissue utilizing autofluorescence. The apparatus includes an endoscope having a distal and proximal end and a light processing unit located at the proximal end of the endoscope. The light processing unit accepts light in a spectral region from a light source and directs the light through the endoscope to the tissue located adjacent the distal end of the endoscope. The light excites autofluorescence in the tissue. Optics located in the distal end of the endoscope collect the excited autofluorescence in a spatially resolved manner and routes it to the light processing unit which processes the emitted light from any reflected excitation light. Imaging detectors receive the emitted light. Each imaging detector is responsive to light in a different spectral band and each generates a separate image. An image is generated according to a plurality of independent measurements.

In another aspect of the invention, an apparatus for sampling tissue includes an endoscope having a sampling device. The sampling device takes a plurality of tissue samples. Captive units are in communication with the sampling device such that each tissue sample is deposited in a separate captive unit.

These and many other features and advantages of the invention will become more apparent from the following detailed description of the preferred embodiments of the invention.

BRIEF DESCRIPTION OF THE DRAWINGS

FIG. 1 is a schematic view of an imaging video endoscopic system incorporating a preferred embodiment of the present invention.

FIG. 2 is a schematic view of the endoscope shown in FIG. 1.

DETAILED DESCRIPTION OF THE PREFERRED EMBODIMENTS

Figure 3:
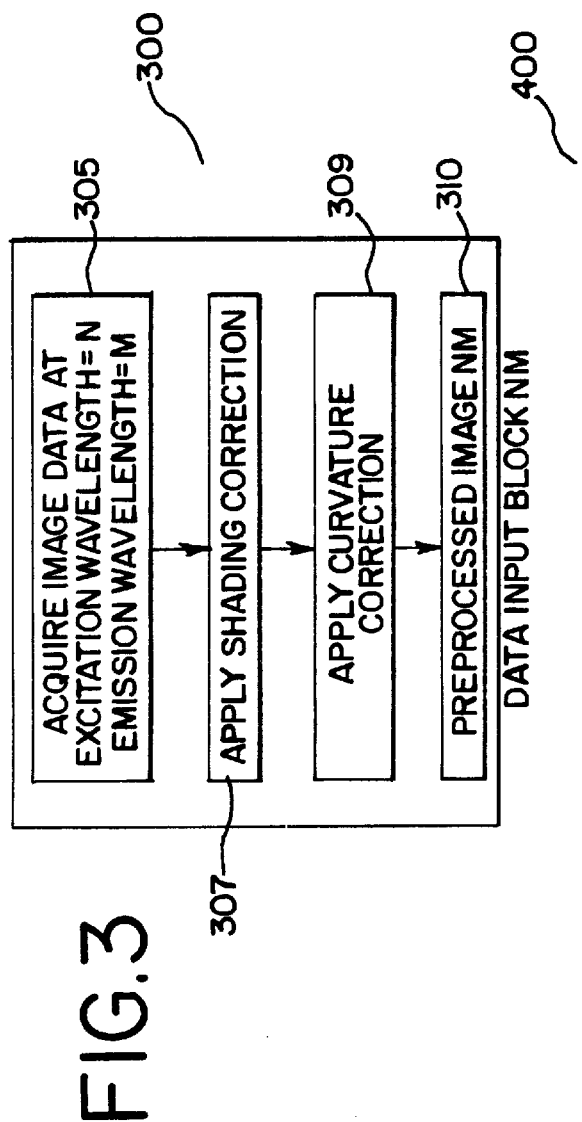
FIG. 3 is a data input block flowchart for generating a preprocessed image.

FIG. 1 illustrates a video endoscopic system 10 for imaging tissue 5. Preferably, the tissue 5 being investigated by the endoscopic system 10 is the tissue of a cervix. Alternatively, the endoscopic system 10 is used to generate an image of any in vivo tissue where use of minimally invasive procedures are advantageous. The endoscopic system 10 utilizes the autofluorescence and reflectance properties of tissues to discriminate between normal and abnormal tissues.

The system 10 includes an endoscope 30, a video monitor 20, a computing device 110 and a light source 40. Alternatively, a second light source 50 is provided and is preferably a white light source. The imaging endoscopic system 10 is suitably sized and shaped for cervical inspection. The endoscope 30, having a distal end 32 and proximal end 31, includes a light processing unit 33, distal optics 35, and imaging detectors 37. Preferably, the light processing unit is either a wavelength division multiplexer or a beam splitter. As will be further discussed with reference to FIG. 2, the endoscope 30 also has a sampling device 260.

The endoscope 30 functions as an imaging reflectance fluorometer or as a reflectance spectrometer depending upon whether the light processing unit 33 is a wavelength division multiplexer or a light processing unit beam splitter, respectively. The light processing unit 33 accepts light in a spectral region which is generated by the light source 40. The light generated by the light source 40 is communicated to the light processing unit by way of fiber optic cable 55. Alternatively, the endoscope includes both a wavelength division multiplexer and a beam splitter may be concatenated to provide both functional modes simultaneously.

The light generated by the light source 40 or 50 is communicated to the light processing unit 33 by way of fiber optic cable 55. The light emitted by light source 40, 50 may encompass a continuum of wavelengths within the ultraviolet, visible and near infrared spectral regions or one or more wavelengths or groups of wavelengths within one or more of these regions. The light processing unit 33, which is used for fluorescence or reflectance measurements, respectively, accepts light of the appropriate spectral distribution from either the first light source 40 or the second light source 50 by way of the fiber optic cable 55. The light is directed from the light processing unit 33 through the endoscope 30 to the distal end 32 where the light illuminates the tissue 5. The endoscope 30 includes optical fibers which can transmit light in both directions between the distal end 32 and the proximal end 31.

The light emerging from the distal end 32 of the endoscope 30 is reflected by and excites autofluorescence in the tissue 5. The light reflected by and the autofluorescent emissions from the tissue 5 is collected by the distal optics 35 contained within the distal end 32 of the endoscope 30. Preferably, this light is collected by the distal optics 35 and transmitted to the proximal end 31 of the scope in a spatially resolved manner where it is routed to the light processing unit 33. The light processing unit 33 separates the light reflected from or emitted by the tissue 5 from the light 41 being directed from either light source 40 or 50 to the proximal end 31 of the scope. The light processing unit further separates light emitted from the tissue 5 from light reflected by the tissue 5. The light emerging from the light processing unit 33 is routed to one or more imaging detectors 45 each of which is responsive to light in a different spectral band. Each imaging detector 45 generates a separate image representative of the specific spectral band associated with that imaging detector 45.

Each generated image is communicated to a computing device 110 for manipulating and storing the images. Preferably, the computing device 110 is in communication with a video monitor 20 wherein the images, either individually or as a composite of a plurality of images can, after the appropriate manipulations, be examined for possible tissue abnormalities.

In a combined image, due to the difference in the wavelengths of autofluorescence between normal and abnormal tissues, various regions of the tissue 5 having abnormalities are visible. In the preferred embodiment where a cervix is being examined, the composite image facilitates localization of any abnormalities on the surface of the cervix. The computing device 110 can alternatively perform image processing and image analysis techniques such as edge enhancement and segmentation which can be applied to these images either singly or in combination thereby facilitating abnormality detection and interpretation. Feature recognition permits electronically establishing visual reference points on the examined tissue and relates to the location of features of interest to these reference points. Furthermore, this capability allows joining multiple contiguous fields of view to produce a panoramic display. Once an area of abnormality in the tissue 5 is detected, the scope 30 may then take a sample of this area.

Information relating to the state of the tissue 5 can be obtained through various methods. For example, in one method of differentiating between normal and abnormal tissues, the intensities of flavinoid autofluorescence at several selected wavelengths is measured. The ratios between these emission intensities for normal and abnormal tissues vary in a characteristic manner. By varying the light transmitted by the light processing device 33 and therefore the excitation wavelengths, various other cellular constituents such as porphyrins can be made to autofluoresce in a diagnostically useful manner, and similarly characteristic ratios can be computed. Computing such a ratio on a pixel by pixel basis from a suitably selected pair of images can produce a derived ratiometric image in which the differences between normal and abnormal tissue are accentuated. These derived images may be further processed by methods such as edge enhancement and segmentation to further accentuate any differentiation.

It is generally known that one can differentiate between normal and abnormal tissues by exciting autofluorescence by illuminating the tissue with light in one wavelength band, measuring the intensity of the light emitted in one or more wavelength bands, computing ratios between those emitted intensities, and discriminating between normality and abnormality on the basis of these ratios. However, since tissue autofluorescence is comprised of emissive contributions from a multiplicity of fluorophores and, even under ideal conditions, the emissions from a single fluorophore tends to be spectrally broad, the autofluorescence spectrum of tissue tends to be relatively undifferentiated with few pronounced features. Furthermore, the fluorescent emission intensities at multiple wavelengths under a single excitation condition are highly correlated. Therefore, the information gained by computing intensity ratios between multiple pairs of emission wavelengths represents only an incremental improvement over that obtained from computing the ratio between a single pair of emission wavelengths.

In a preferred embodiment, the system 10 utilizes information obtained at a multiplicity of emission wavelengths generated at a multiplicity of excitation wavelengths, each wavelength combination selected to, in and of itself, to maximize discriminatory power between normal and abnormal tissues. Therefore, instead of relying upon a single measurement to obtain the desired differentiation, system 10 utilizes multiple independent measurements that are combined to obtain substantially improved discrimination. Furthermore, as described below, system 10 allows the results obtained through the use of multiple independent measurement techniques to be combined to further improve the robustness of the discrimination between normal and abnormal tissues. The use of statistically based classification functions and multi-dimensional pattern matching techniques to effect this merging and interpretation on the multiplicity of independent data sets furthers this goal.

Preferably, additional information is derived and interpreted by acquiring the autofluorescence signals in a time resolved manner. The relaxation times and fluorescent lifetimes of different fluorophores, which are determined from time resolved measurements, differ substantially between fluorophores. The various relaxation times can therefore provide an indication of a fluorphore's identity. These parameters are frequently influenced by the environment surrounding the fluorophore in ways that, in turn, reflect the normality or abnormality of the surrounding tissue.

In another preferred embodiment, reflectance spectrometry provides yet another means of probing tissue status as changes in the tissue status are often evidenced by the changes in colored constituents of the tissue. Although normally practiced in the visual spectral region, reflectance spectrometry can be extended into the near infra red as well as ultraviolet. Reflectance spectrometry is extended to a depth where the incident light penetrates the tissue 5 sufficient enough such that additional tissue information can be obtained. This information could include such characteristics as the concentrations of certain metabolites and the degree of blood oxygenation. Raman scattering could also be used because of increased incident light penetration and the fact that there is a relative scarcity of fluorophores having excitation bands in the near infra red.

The previously discussed methods can be used individually as a means of detecting, and in some cases interpreting differences in tissue status. Unfortunately, the nature of human tissue is such that the application of any one of these methods produces an overabundance of data, most of which is extraneous to the intended measurement. The primary contributor to this situation is that tissues contain an extensive and diverse assortment of fluorescent species. Many of the fluorescent species are present in high concentrations and have excitation bands distributed throughout the ultraviolet and most of the visible spectral regions.

As previously discussed, the emission band of one fluorophore may overlap the excitation band of another fluorophore thereby leading to energy transfer between the two. Consequently, there is a distinct possibility that emissions from one fluorophore may excite another. The net effect is that optically exciting a tissue sample having a wavelength in the ultraviolet or visible wavelength region will cause the tissue to autofluoresce over a broad spectral range. As these emissions typically are composed of contributions from multiple fluorophores, the autofluorescence spectrum is complex and difficult to resolve. This, in turn, makes it difficult to obtain a robust discrimination between tissue states through the use of a single method.

A preferred embodiment of the present invention resolves these problems by applying methods that have been developed for applications such as the mapping of natural resources and military reconnaissance. These "multispectral" methods in effect "fuse" or combine the outputs of multiple sensing modalities to obtain a result that is considerably more robust than the results obtained using any one modality independently.

For example, the classical approach to determining tissue autofluorescence is to treat the tissue as a single homogenous entity, excite it at one wavelength and measure the emissions at another wavelength. This sort of measurement is critically dependent upon using a stable, well-calibrated instrument and upon having negligible, or at least relatively low extraneous background fluorescence at the emitted wavelength. In contrast to the classical approach, robust determinations are preferably made by measuring the fluorescence at two or more emission wavelengths. The use of multiple emission wavelengths performs internal consistency checks. Calculating ratios between the emission intensities provides another means for discriminating between changes of interest from background noise.

Because the classical approach treats the tissue 5 as a single homogeneous entity, the classical approach does not provide the spatial resolution needed to determine whether an abnormality is localized or whether an abnormality is widely distributed. Generating the fluorescence measurements described above at multiple discrete points on an image provides the spatial information needed to determine the location of any abnormalities.

In an alternative embodiment, multiple excitation wavelengths are used and other techniques are applied such as time resolved spectrometry. Each additional parameter applied supplies unique information that can be used to discriminate between tissue states. However, the multiple parameters provide redundant or extraneous information. Adding derived parameters such as intensity ratios to the data set can define or reflect significant tissue characteristics that can, in turn, facilitate interpretation.

The preferred approach to interpreting this voluminous mass of data is "preponderance of evidence" wherein each data set is interpreted by the computing device 110 independently of any other data set. A majority vote method is applied to the collection of conclusions derived from the data sets. An alternative, more sophisticated approach applies a multivariate classifier or discriminate function that combines information from the various data sets in a prescribed, and statistical manner. A single composite result is then obtained. Such methods are usually applied at each point or pixel of an image in a spatially resolved image. Incorporating multiple lines of evidence into a single determination works to filter out extraneous and redundant information while improving the robustness of the final determination.

In another preferred embodiment, more advanced techniques such as contour following are used. For example, if the data sets are viewed as a stack of image planes each of which collected under different defined conditions, a contour through the stack describes the changes or evolution of the signal level at each pixel as a function of the measurement parameters. The shape or shapes of the contours provide additional discrimination between different possible interpretations.

The endoscopic system 10 of FIG. 1 acquires data under a multiplicity of conditions as previously described. The computing device 110 evaluates the image data acquired under these conditions. The generated data is interpreted, not in isolation of each individual generated parameter, but in its entirety as a composite whole. This preferred composite analysis improves the accuracy and robustness of the final determination as to the normality or abnormality of the tissue 5. Due to the large amounts of data involved in this preferred composite type of approach, it may be desirable to apply fuzzy logic. Alternatively, a neural network or other "self-teaching" method can be used for the interpretation of either the entire data set or to subsets thereof.

In addition to the individual images taken under multiple conditions, the second light source 50 is used to generate a "white light" image by directly using broad band illumination. Alternatively, the white light image is synthesized from multiple narrow band images.

In addition to its potential relating to its diagnostic utility, the white light image allows identifying visual positional reference features within the field of view of the endoscope. In a preferred embodiment, the white light image is overlaid with markers. The markers designate certain reference features, locations or regions of the tissue that analytical methods such as those described above have identified as being abnormal or suspect. Such reference features facilitate the ability of an examining physician to return at a later time to a previously investigated location of the cervix. For example, if the physician performs a preliminary test to evaluate a sample recently taken and subsequently determines that, for one reason or another, a follow-up sample is required, the location from where the initial sample was taken can be quickly and accurately identified.

Preferably, two types of interpreting schemes are used to interpret the multiplicity of data sets generated by the system 10. Before these interpreting schemes are described, however, the processing of the generated data sets will be discussed.

FIG. 3 illustrates a data input block flow chart 300 which shows how a preferred embodiment of the present invention generates a preprocessed image 310. First, image data 305 is acquired at the image acquiring step 305. The image data relates to a particular excitation wavelength N and a particular emission wavelength M which together define an initial image NM. Once the image data and therefore the initial image NM is acquired, shading correction is applied during a shading correction step 307. After the image has been corrected for shading, curvature correction is applied during a curvature correction step 309. The preprocessed image NM is then defined as an image block NM. Various image blocks can be similarly generated for each excitation wavelength N and each emission wavelength M pair. Preferably, a plurality of image blocks NM are generated and configured as data input blocks, which in turn are used to generate a composite image. A resulting preprocessed image NM 310 is then used generate a plurality of ratio blocks as shown in FIG. 4.

Figure 4:
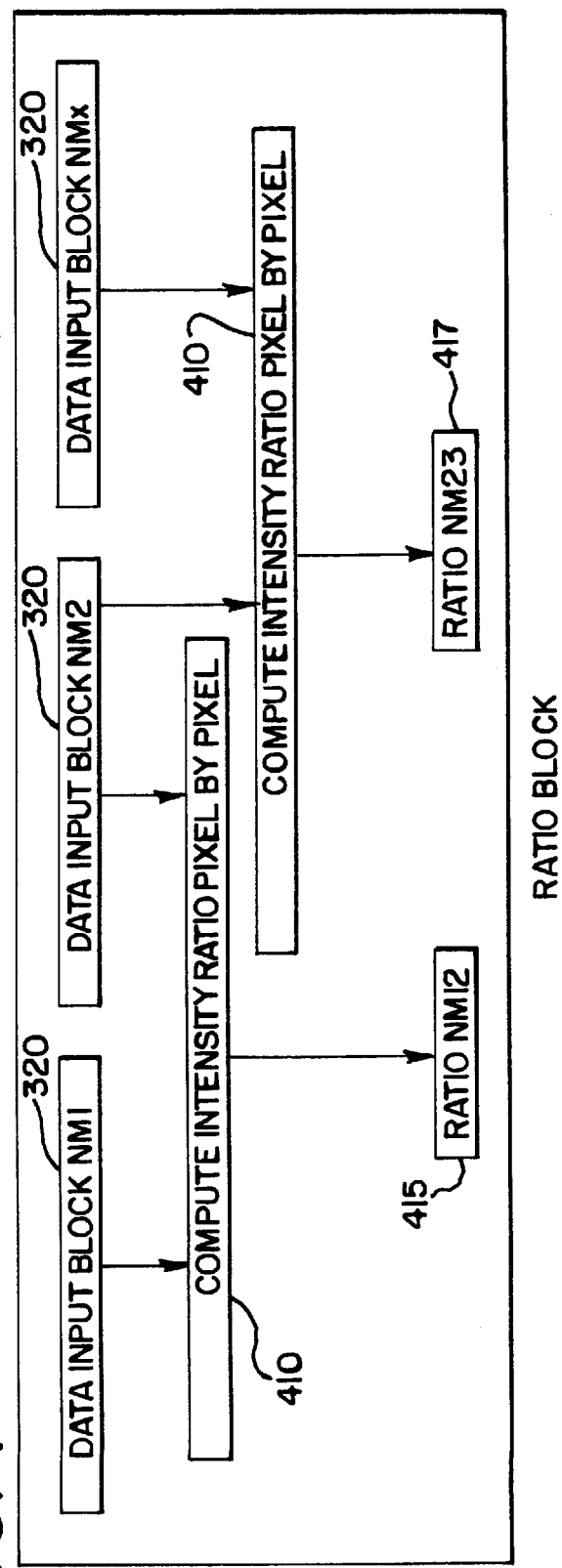
FIG. 4 illustrates a ratio block flowchart for generating a composite ratio image from the data input blocks generated by the flowchart shown in FIG. 3.

FIG. 4 illustrates a ratio block flow chart 400 for generating a composite ratio image from the data input blocks 320 generated in FIG. 3. First, the ratio block flowchart 400 generates a plurality of intensity ratios 410 during the intensity ratio step. An intensity ratio 415 is computed for varying data input blocks 320. For example, a first intensity ratio Ratio NM12 415 is computed for the data input blocks NM1 and NM2. A second intensity ratio Ratio NM23 417 is computed for the data input blocks NM2 and NM3. This process is repeated for each different emission wavelength M. Preferably, an intensity ratio is computed for each pixel of the resulting image. The generation of intensity ratios are repeated for each pair of excitation wavelengths N and emission wavelengths of interest M. Preferably, at least two emission wavelengths M for each excitation wavelength are generated. The resulting matrix of generated intensity ratios is then used to generate a ratio image which is then interpreted to analyze the state of the tissue.

In a preferred embodiment, a first approach to interpreting the ratio image applies a first and a second threshold value to each pixel in the ratio image. The ratio image is then segmented, categorized or defined into various regions. Preferably, the pixels of the ratio image are segmented into either normal, suspect or abnormal regions. Preferably, the first and the second threshold values are empirically derived based upon the statistical distribution of ratio values in a large number of reference images. For example, an upper (Tu) and a lower (Th) threshold are defined and are used for image interpretation.

For example, if a ratio value at a given pixel position is defined as R, then three scenarios are possible. First, if the ratio value R is greater than the upper threshold Tu, then the pixel is classified as being abnormal. Second, if the ratio value R is greater than the lower threshold Th but less than the upper threshold Tu, then the pixel is classified as being suspect. Third, if ratio value R is less than the lower threshold Th, then the pixel is classified as being normal. A resulting image can then be generated and analyzed according to pixel classification.

In another preferred embodiment, a segmentation algorithm is applied to interpret the ratio image. First, a search is made of the entire ratio image for local minima Alternatively, a search is made of the entire ratio image for local maxima. In the case where a search for local minima is made, at each local minimum found, a temporary threshold value is defined and equated to the ratio value at the minimum plus one. The ratio values at all neighboring pixel locations are then examined. If the value at the neighboring pixel being examined is less than or equal to the temporary threshold value, the neighboring pixel is tagged with the identifier for the minimum with which it is now associated. If the pixel has been previously tagged, the designation is not changed. This cycle is repeated until all pixels making up the ratio image are "tagged." All pixels having the same tag value are considered to belong to the same region, whether that region is defined as normal, abnormal or suspect.

Preferably, a conventional matched filter is applied to detect particular features or feature shapes within the initial preprocessed image or the ratio image or alternatively in the threshold renditions of these images. Filtering, usually in combination with dilation and erosion, smoothes the boundaries between regions and removes noise from the resulting images.

The preprocessed images generated as described in FIG. 3 or the ratio image generated as described with reference to FIG. 4 can also be interpreted using a linear or statistical classifier. Preferably, the classifiers are of the form: Figure of Merit=F(I1, I2, I3, . . . In) where I represents pixel values in the preprocessed image or the ratio image. Preferably, the function "F" is determined by the multivariate statistical analysis of a large population of reference images. Standard statistical tests for significance determine which images or pixels are used in interpreting measurements made on any particular type of tissue image. The multivariate statistical analysis effectively determines how much weight should be given to each of the remaining parameters.

FIG. 2 illustrates the details of the endoscope 30 shown in FIG. 1. Endoscope 30 includes a sheathing member 205, a distal end 32 and a sampling device 220 located at the distal end 32. The sampling device 220 is used to extract samples from the tissue 5 under investigation. Preferably, the sampling device 220 is manipulated by a physician while performing autofluorescence imaging as previously discussed. The sampling device 220 is also steerable. By steerable, it is meant that the sampling device 220 is rotatable, pivotable and retractable within the endoscope sheathing 205 in such a manner that the sheathing 205 does not need to be manipulated or controlled.

Preferably, the sampling device 220 is configured as a brush 225 having a plurality of sampling members 226. To take a sample of tissue 5, the sampling device 220 is manipulated and steered to a location adjacent the suspect tissue 5. The brush 225 rotates preferably in a counter-clockwise direction. The sampling device 220 or more preferably the brush 225 extends towards the tissue 5 such that the sampling members 226 come into contact with the tissue 5. The rotating sampling members 225 securely remove an outer cell layer of the examined tissue 5.

Alternatively, the sampling device 220 includes a sampling ribbon, an unwind reel and a rewind reel. Before any samples have been taken, the entire sampling ribbon resides on the unwind reel. As samples are taken, a predetermined length of the sampling ribbon is unwound from the unwind reel onto a rewind reel. During sampling, a portion of the ribbon comes into contact with the tissue 5 thereby securing a tissue sample. As subsequent samples are taken, the rewind reel takes up the sampling ribbon segment containing the sampled tissue. Another sample can then be taken. Once the entire sampling ribbon is completely transferred from the unwind to the rewind reel, the sampled tissue stored on the ribbon of the rewind reel can be taken out of the endoscope 30 and tested. The sampling ribbon can then be tested at the physician's facility and then sent to a laboratory for further testing.

During the imaging procedure previously described with respect to FIG. 1, the sampling device 220 remains in a retracted state. In this retracted state, the sampling device 220 remains inside the sheathing 205 of the endoscope 200 and decreases any interference the sampling device 220 may create during imaging. Once the physician operating the scope 30 determines that a sample of the investigated tissue 5 should be taken, the sampling device 220 is extended beyond the distal end of the scope 30, towards the tissue 5. After a sample is taken, the sampling device 220 can then be retracted back within the distal end 206 of the endoscope 200. Further imaging or sampling can then take place.

Preferably, the sampling device 220 removes a plurality of tissue samples from the tissue in a sequential order. This enables the operator of the device to collect a set of samples from either the same suspect location or alternatively from a variety of different areas. The ability to take a plurality of tissue samples during one minimally invasive procedure results in a number of benefits. For example, where a plurality of samples are taken from the same or different location, specimens will generally have an enhanced probability of containing abnormal cells. Moreover, having a collection of samples taken from an abnormal tissue area increases the probability that the samples contain a portion of the suspect tissue which initially gave rise to the determination that a sample should be collected. Having a set of samples which are not taken blindly also enables the physician to revisit and perform further investigation of various, previously investigated suspect areas.

Preferably, once the sampling device 220 extracts a sample, the sample is drawn into a captive unit 260. Preferably, the captive unit 260 is a sterile container such as a sleeve, capsule, or like device. More preferably, the endoscope 30 contains a plurality of captive units 260 such that each time a tissue sample is taken, the sample is placed in its own, separate sterile captive device 260. The captive device 260 can be provided with an identification means such as a label, print-out or other similar type of identifier. The captive device 260 is preferably detachable from the sampling device 220 and therefore the endoscope 30 such that the captive units 260 can be used as storage containers. The storage container simplifies the transporting, marking and identifying various aspects of the sample.

Preferably, the captive units 260 are disposable, so that, after final testing of a sample, a captive unit 260 originally containing the sample can be disposed of. Alternatively, the captive unit 260 is reusable such that it can be repeatedly sterilized and reused.

The extracted samples contained within the captive units 260 can be initially examined at the physician's location and then sent to a laboratory for further testing. Preferably, the physician performs an initial test on the sample. The initial test can be used to determine whether the samples are indeed samples taken from the investigated suspect tissue. The initial test also enables the physician to make a relatively quick determination as to whether any additional samples of the patient are required. Local testing also enables the physician to determine relatively quickly whether the tissue is actually abnormal. This is an important consideration since it has been documented that over ninety percent of Pap smear tests sent to labs for testing result in a negative result. Consequently, by providing the physician with a preliminary screening test for determining whether the sample contains abnormalities provides a number of advantages.

For example, the patient is not required to go through an additional two or three weeks of anxiety waiting for the results of the test. The samples removed by way of the previously discussed method can also be examined by any standard method. The initial test is performed by the physician by taking a portion of the sample tissue and smearing it on a slide. This slide can then be analyzed at the same location where the sample was taken. If this preliminary test or screen performed by the physician results in an abnormal reading, the entire captive unit can then be transported to a laboratory where the standard analysis can be conducted.

By being able to take a plurality of samples, a "map" of cervix sampling locations is generated. By mapping previously sampled locations and by using of the previously discussed visual reference points, these same sampling locations can be revisited during subsequent follow-up examinations. In addition, by taking a plurality of tissue samples and thereby enhancing the probability of detecting and collecting abnormal cells, the proposed system also provides a cost effective and efficient means for follow up testing based on an abnormal Pap smear.

One preferred means of performing an immediate examination of a sample is to subject the sample to fluorimetric measurements similar to those described above. In this preferred method, an aliquot of the sample taken by the sampling device may be tested in its current state (i.e., "as is"). Alternatively, the sample is suspended within a captive unit in an appropriate fluid medium. In this alternative embodiment, the sampling device places each sample into a captive unit holding both the extracted sample and a fluid medium. This method eliminates a number of the problematic areas normally associated with the preparation, transportation and testing of Pap test samples. Moreover, this method reduces the number of samples which must be sent out for costly analysis to an off-site investigation. In addition, because the number of Pap smear false positive test results will be decreased, anxiety of women waiting for follow up test results will be decreased.

As the conditions surrounding the proposed methods of Pap test re-testing are better defined and controlled than those used for the in-situ identification of sampling regions, a positive second test provides a high probability of confirming that the sampled tissue was abnormal. This information can then be used as a means of verifying that the intended sample was indeed taken and could be used to determine which samples should be subjected to a more vigorous analysis.

While the invention has been described in conjunction with the presently preferred embodiments of the invention, persons of skill in the art will appreciate that variations may be made without departure from the scope and spirit of the invention. This true scope and spirit is defined by the appended claims, as interpreted in light of the foregoing.

We claim:

1. An apparatus for imaging tissue using autofluorescence, comprising, in combination:

an endoscope having a distal end and a proximal end, whereby the tissue may be located at the distal end;

a light source for generating a first light;

a light processing unit located at the proximal end of the endoscope for receiving the first light and directing the first light to the tissue, the first light arriving at the tissue and exciting autofluorescence in the tissue, a second light thereby being produced, the second light comprising light emitted from the tissue and light reflected from the tissue, the emitted light representing a spatial distribution of the autofluorescence;

optics located in the distal end of the endoscope, the optics receiving the second light and providing the second light to the light processing unit, the light processing unit separating the second light into the emitted light and the reflected light;

a plurality of imaging detectors for receiving the emitted light, each imaging detector being responsive to light in a different spectral band and therefore receiving a corresponding spectral band of the emitted light, each imaging detector producing an image of the tissue in the imaging detector's corresponding spectral band, each image comprising a plurality of pixels each representing a respective visible portion of the tissue and having a corresponding pixel value;

means for functionally combining the pixel values of spatially corresponding pixels in a plurality of said images on a pixel-by-pixel basis so as to produce at least one set of derived pixel values, each derived pixel value in the at least one set of derived pixel values corresponding to a respective derived pixel that represents a respective visible portion of the tissue; and means for interpreting each of the at least one set of derived pixels on a pixel-by-pixel basis, the means for interpreting including means for comparing each derived pixel value in the set to at least one threshold value and, based on the comparison, establishing a characterization of the visible portion of the tissue represented by the derived pixel that corresponds to the derived pixel value.

2. An apparatus as claimed in claim 1, wherein the at least one set of derived pixels comprises multiple sets of derived pixels; and wherein the apparatus further comprises means for categorizing each of at least a plurality of visible portions of the tissue represented by spatially corresponding pixels in a plurality of the sets of derived pixels, based on the characterizations established for the visible portion, so as to produce a categorization respectively of the visible portion.

3. An apparatus as claimed in claim 2, wherein the categorization of a visible portion is based on a majority vote of the characterizations established for the visible portion and defines a majority vote pixel corresponding to the visible portion.

4. An apparatus as claimed in claim 3, further comprising a video monitor for displaying an image defined by the majority vote pixels corresponding to a plurality of visible portions of the tissue.

5. An apparatus as claimed in claim 1, wherein the means for interpreting comprises a computing device.

6. An apparatus as claimed in claim 1, wherein the characterization of each visible region is selected from the group consisting of normal, abnormal and suspicious.

7. An apparatus as claimed in claim 1,
wherein each pixel value represents a measure of intensity of the emitted light; and
wherein the means for functionally combining comprises means for establishing a ratio of the pixel values of spatially corresponding pixels.

8. An apparatus as claimed in claim 3,
wherein each pixel value represents a measure of intensity of the emitted light; and
wherein each derived pixel value comprises a ratio of two pixel values.

9. An apparatus as claimed in claim 1, wherein each pixel value comprises a measurement of time selected from the group consisting of a relaxation time of the emitted light and a fluorescent lifetime of the emitted light.

10. An apparatus as claimed in claim 1, wherein the means for interpreting each of the at least one set of derived pixels operates to independently interpret each of the at least one set of derived pixels.

11. An apparatus as claimed in claim 1, further comprising means for marking a visible light image of the tissue with marks representing the characterizations of visible portions of the tissue.

12. An apparatus as claimed in claim 1, further comprising means for image processing each of the at least one set of derived pixels.

13. An apparatus as claimed in claim 12, wherein the means for image processing comprises means for performing edge enhancement.

14. An apparatus as claimed in claim 12, wherein the means for image processing comprises means for performing segmentation.

15. An apparatus as claimed in claim 1, further comprising a video monitor for displaying an image comprising at least one set of the derived pixels.

16. A method for imaging tissue using autofluorescence, the method comprising, in combination:
generating a first light;
applying the first light via an endoscope to the tissue, the first light exciting autofluorescence in the tissue, a second light thereby being produced, the second light comprising emitted light emitted from the tissue and reflected light reflected from the tissue, the emitted light representing a spatial distribution of the autofluorescence;
extracting the emitted light from the second light;
receiving the emitted light at a plurality of imaging detectors, each imaging detector being responsive to light in a different spectral band and therefore receiving a corresponding spectral band of the emitted light, each imaging detector producing an image of the tissue in the imaging detector's corresponding spectral band, each image comprising a plurality of pixels each representing a respective visible portion of the tissue and having a corresponding pixel value;
functionally combining the pixel values of spatially corresponding pixels of a plurality of said images on a pixel-by-pixel basis so as to produce at least one set of derived pixel values, each derived pixel value in the at least one set of derived pixel values corresponding to a respective derived pixel that represents a respective visible portion of the tissue; and
interpreting each of the at least one set of derived pixels on a pixel-by-pixel basis, including comparing each derived pixel value in the set to at least one threshold value and, based on the comparison, establishing a characterization of the visible portion of the tissue represented by the derived pixel that corresponds to the derived pixel value.

17. A method as claimed in claim 16, further comprising cooperatively evaluating a plurality of the at least one set of derived pixels, including taking a majority vote of the characterizations for the visible portion for each visible portion of tissue represented by spatially corresponding pixels in the plurality of sets, whereby the majority vote for each visible portion defines a majority vote pixel.

18. A method as claimed in claim 17, further comprising displaying a set of the majority vote pixels as a video image on a video monitor.

19. A method as claimed in claim 16, wherein the characterization of a visible portion is selected from the group consisting of normal, abnormal and suspicious.

20. A method as claimed in claim 16, wherein each pixel value comprises a measurement of time selected from the group consisting of a relaxation time of the emitted light and a fluorescent lifetime of the emitted light.

21. A method as claimed in claim 16, wherein interpreting each of the at least one set of derived pixels comprises independently interpreting each set.

22. A method as claimed in claim 16, further comprising marking a visible light image of the tissue with marks representing the characterizations of visible portions of the tissue.

23. A method as claimed in claim 16, further comprising modifying an aspect of each image, the aspect of a given image being selected from the group consisting of shading and curvature.

24. A method as claimed in claim 16, further comprising performing edge enhancement on each of the at least one set of derived pixels.

25. A method as claimed in claim 16, further comprising performing segmentation on each of the at least one set of derived pixels.

26. A method as claimed in claim 16, further comprising presenting a selection of the at least one set of derived pixels as a video image on a video monitor.

* * * * *